United States Patent [19]

Binderup et al.

[11] Patent Number: 5,130,304
[45] Date of Patent: Jul. 14, 1992

[54] N-HETEROCYCLIC PROPYLIDENE-1,1-BISPHOSPHONIC ACIDS, THEIR PRODUCTION AND A PHARMACEUTICAL COMPOSITION

[75] Inventors: Ernst T. Binderup, Tåstrup; Sven Liisberg, Vedbæk, both of Denmark

[73] Assignee: Leo Pharmaceutical Products Ltd., Ballerup, Denmark

[21] Appl. No.: 543,773

[22] PCT Filed: Mar. 29, 1989

[86] PCT No.: PCT/DK89/00071
§ 371 Date: Oct. 9, 1990
§ 102(e) Date: Oct. 9, 1990

[87] PCT Pub. No.: WO89/09775
PCT Pub. Date: Oct. 19, 1989

[30] Foreign Application Priority Data

Apr. 7, 1988 [GB] United Kingdom ............... 8808138

[51] Int. Cl.$^5$ ............ A61K 31/675; C07F 9/572
[52] U.S. Cl. ........................................ 514/91; 548/413
[58] Field of Search ............... 548/413, 414; 514/91

[56] References Cited

U.S. PATENT DOCUMENTS 4,871,720  10/1989  Jaeggi .................... 514/79

FOREIGN PATENT DOCUMENTS 1002300  3/1983  U.S.S.R. .

OTHER PUBLICATIONS

March, J. *Advanced Organic Chemistry* Third Edition John Wiley and Sons, Inc., 1985, p. 689, 664–665.

*Primary Examiner*—Mary C. Lee
*Assistant Examiner*—Michael G. Ambrose
*Attorney, Agent, or Firm*—Cushman, Darby & Cushman

[57] ABSTRACT

The present invention relates to compounds of formula in which $R_1$-$R_8$ can be the same or different and stand for hydrogen or a straight or branched aliphatic $C_1$-$C_{10}$ hydrocarbon radical. In addition, $R_3$ when taken together with either $R_1$ or $R_5$ can form a saturated aliphatic 5-, 6-or 7-membered ring, which may be substituted with one or more $C_1$-$C_4$-alkyl radicals. The present compounds are effective e.g. in drugs influencing calcium metabolism.

9 Claims, No Drawings

N-HETEROCYCLIC PROPYLIDENE-1,1-BISPHOSPHONIC ACIDS, THEIR PRODUCTION AND A PHARMACEUTICAL COMPOSITION

The present invention relates to hitherto unknown compounds useful in the human and veterinary therapy, to pharmaceutically acceptable salts, to method for producing said new compounds, to pharmaceutical compositions containing the new compounds, to dosage units of the compositions, and to methods of treating patients using said compositions and dosage units.

The present compounds have the formula I

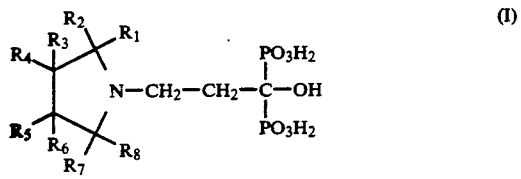

in which $R_1$–$R_8$ can be the same or different and stand for hydrogen or a straight or branched aliphatic $C_1$–$C_{10}$ hydrocarbon radical.

In addition, $R_3$ when taken together with either $R_1$ or $R_5$ can form a saturated aliphatic 5-, 6- or 7-membered ring, which may be substituted with one or more $C_1$–$C_4$-alkyl radicals.

In particular, $R_1$–$R_8$ stand for hydrogen or $C_1$–$C_4$-alkyl.

The invention comprises all possible stereoisomeric forms of compounds of formula I as well as mixtures thereof.

As stated above, the invention also relates to salts of the compounds of formula I which are tetrabasic acids and thus form mono-, di-, tri-, and tetrabasic salts with bases. As examples of salts formed with pharmaceutically acceptable, non-toxic bases, mention may be made of alkali metal salts and alkaline earth metal salts, such as lithium, sodium, potassium, magnesium, and calcium salts, as well as salts with ammonia and suitable non-toxic amines, such as lower alkylamines, e.g. triethylamine, lower alkanolamines, e.g. diethanolamine or triethanolamine, procaine, cyclo-alkylamines, e.g. dicyclohexylamine, benzylamines, e.g. N-methylbenzylamine, N-ethylbenzylamine, N-benzyl-β-phenethylamine, N,N'-dibenzylethylenediamine or dibenzylamine, and heterocyclic amines, e.g. morpholine, N-ethylpiperidine and the like.

In addition to the above, in vivo easily hydrolyzable esters are also envisaged. Being tetrabasic acids, the compounds of formula I can form mono-, di-, tri-, or tetraesters.

Examples of such ester forming residues are alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxy)ethyl of four to six carbon atoms, 1-(alkoxycarbonyloxymethyl of four to seven carbon atoms, 1-methyl-1-(alkoxycarbonyloxy)ethyl of five to eight carbon atoms, 3-phthalidyl, 4-crotono-lactonyl, γ-butyrolacton-4-yl, (2-oxo-1,3dioxolen-4-yl)-methyl, (5-methyl-2-oxo-1,3-dioxolen-4-yl)methyl, and (5-phenyl-2-oxo-1,3dioxolen-4-yl)methyl as well as dialkylamino-alkyl, acetonyl, and methoxymethyl.

A number of bisphosphonic acid derivatives are known for use within the present field. SU 1002300 describes the preparation of 1-hydroxy-3-(4'-morpholinyl)-propylidene-1,1-bisphosphonic acid and 1-hydroxy-3-(1'-piperidyl)-propylidene-1,1-bisphosphonic acid and mentions the possible use of these compounds as complex forming agents and in the preparation of drugs influencing calcium metabolism.

The normal bones are living tissues undergoing constant resorption and redeposition of calcium, with the net effect of maintenance of a constant mineral balance. The dual process is commonly called "bone turnover". In normal growing bones, the mineral deposition exceeds the mineral resorption, whereas in certain pathological conditions, bone resorption exceeds bone deposition resulting in osteoporosis or in hypercalcemia, for instance due to malignancy or primary hyperparathyroidism. In other pathological conditions the calcium deposition may take place in undesirable amounts and areas leading to e.g. osteoarthritis, rheumatoid arthritis, kidney or bladder stones, atherosclerosis, and Paget's disease which is a combination of an abnormal high bone resorption followed by an abnormal calcium deposition.

The compounds of the present invention are able to increase bone mass by reducing bone resorption. The increase in bone mass is measured by the increase in tibia metaphyseal weight.

Experiments in rats have shown that the compounds of the present invention are surprisingly potent in increasing tibia metaphyseal weight. The table below shows that both the weight and the calcium content of the tibia metaphysis can be considerably increased by subcutaneous administration of the compound of Example 2 (EB 1053, formula I, $R_1$–$R_8$=H). EB 1053 is compared with APD (3-amino-1-hydroxy-propylidene-1,1-bisphosphonic acid), which has recently been made available as the second and most active bisphosphonate on the market (Etidronate - 1-hydroxyethylidene-1,1-bisphosphonic acid has been on the market for a number of years).

| Compound | Dosage μmol/kg/day s.c. (7 days) | Tibia metaphyseal weight % change compared to control | Calcium mg/metaphysis % change compared to control |
|---|---|---|---|
| EB 1053 | 1.6 | +50 p < 0.001 | +62 p < 0.001 |
| | 0.16 | +44 p < 0.001 | +64 p < 0.005 |
| | 0.016 | +24 p < 0.001 | +25 p < 0.001 |
| | 0.0016 | +3 n.s. | +2 n.s. |
| APD | 1.6 | +24 p < 0.001 | +29 p < 0.05 |
| | 0.16 | +12 n.s. | +18 n.s. | statistical analysis by Students t-test,
n.s. = not significant

It is seen from the table that EB 1053 is considerably more potent than APD. In addition, experiments in rats have shown that EB 1053 is less toxic than APD. Thus EB 1053 has a better therapeutic index than APD.

A further advantage of the high potency of the present compounds is that the low dosage levels needed are less likely to cause gastro-intestinal discomfort which sometimes is associated with oral administration of large doses of bisphosphonates.

Also, the high potency of the compounds make them especially suited for alternative administration routes, e.g. intranasal or transdermal delivery.

The compounds of the present invention may be prepared by reacting a compound of formula II

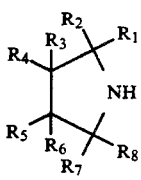

in which $R_1$–$R_8$ have the meanings defined above with a compound of formula III

in which $R_9$ is a lower alkyl radical to form a compound of formula IV

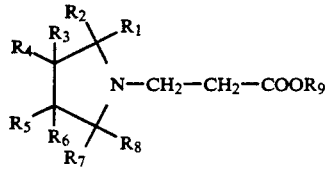

which subsequently is hydrolyzed to the corresponding free acid ($R_9 = H$). The free acid is then reacted with phosphorous acid and either phosphorus oxychloride or phosphorus trichloride followed by aqueous hydrolysis to form a compound of formula I.

The present compounds are as mentioned above intended for use in pharmaceutical compositions which are useful in the treatment of osteoporosis, rheumatoid arthritis and other arthritis disorders, atherosclerosis, hypercalcemia due to malignancies or primary hyperparathyroidism, Paget's disease, and other conditions with an abnormal calcium balance.

The present compounds may also be used in toothpastes in order to prevent calcium deposition in the form of dental calculus or in order to protect against calcium resorption due to acid dissolution.

The amount required of a compound of formula I (hereinafter referred to as the active ingredient) for therapeutic effect will, of course, vary both with the particular compound, the route of administration and the mammal under treatment. A suitable dose of a compound of formula I is 0.001 to 15 mg per kilogram body weight, the preferred dosage being 0.008–0.3 mg/kg bodyweight/day by parenteral administration and 0.1–10 mg/kg bodyweight/day by oral administration.

While it is possible for an active ingredient to be administered along as the pure compound, it is preferable to present it as a pharmaceutical formulation. Conveniently, the active ingredient comprises from 0.01% to 99.9% by weight of the formulation. Conveniently, dosage units of a formulation contain 0.25–16 mg of the active ingredient when to be given parenterally, and 3–600 mg when to be given orally, said dosage units to be administered once or more times daily, or with suitable intervals (days, weeks or months).

The formulations include those in a form suitable for oral, rectal, parenteral (including subcutaneous, intramuscular and intravenous), nasal, transdermal, or topical administration.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations for nasal administration may take a solid, liquid or semi-liquid form, optionally together with an absorption enhancer (e.g. sodium tauro-24, 25-dihydrofusidate).

The compositions may further contain other therapeutically active compounds usually applied in the treatment of the above mentioned pathological conditions, for instance vitamin $D_2$ and $D_3$ and hydroxylated derivatives, e.g. $1\alpha$-hydroxy-vitamin $D_3$, $1\alpha$-hydroxy-vitamin $D_2$, $1\alpha,25$-dihydroxy-vitamin $D_3$ $1\alpha,25$-dihydroxy-vitamin $D_2$, calcitonin (human, porcine or salmon), mitramycin, sodium fluoride, estrogens, and non-steroid antiinflammatory drugs, e.g. actylsalicylic acid, indomethacin, and naprosyn.

According to the invention, the present compounds are administered to a patient suffering from one of the above mentioned pathological conditions in a daily or intermittent dosage (for adults) from 250 μg–600 mg.

The invention will now be further described in the following non-limiting Examples:

EXAMPLE 1

3-(1'-Pyrrolidinyl)-propanoic acid, hydrochloride

A mixture of ethyl 3-(1'-pyrrolidinyl)-propanoate (102.6 g) and 6 N hydrochloric acid (340 ml) was refluxed for 4 hours. After cooling and evaporation to dryness in vacuo, the residue was dissolved in glacial acetic acid and the solution evaporated in vacuo. The crystalline residue was stirred with glacial acetic acid, filtered and washed with glacial acetic acid and ether. Drying in vacuo gave the analytically pure title compound. M.p. 175°–177° C.

EXAMPLE 2

1-Hydroxy-3-(1'-pyrrolidinyl)-propylidene-1,1-bisphosphonic acid (EB 1053)

Phosphorous acid (27.5 g) was dissolved in phosphorus oxychloride (30.7 ml) and 3-(1'-pyrrolidinyl)-propanoic acid, hydrochloride (30 g) was added. The mixture was heated slowly—hydrogen chloride gas escaped—to 100° C. where the temperature was kept for 2 hours. The reaction mixture (a foam) was treated with water (178 ml) and refluxed for 3 hours. After cooling and evaporation to dryness in vacuo, the residue was taken up in water (35 ml) and methanol (90 ml) was added to crystallization. After cooling and filtration, the colorless crystalline product was washed with methanol and ether and dried in vacuo.

M.p. 235° C. (dec.).

Microanalysis: Calc.: C: 29.08; H: 5.99; N: 4.84; P: 21.42

Found: C: 28.93; H: 5.92; N: 4.91; P: 21.38

¹H-NMR (D₂O, HDO=4.66 ppm as reference): δ : 1.70–2.05 (m, 4H); 2.10–2.30 (m, 2H); 2.80–3.00 (m, 2H); 3.30–3.40 (t, 2H) and 3.45–3.65 (m, 2H) ppm.

¹³C-NMR (D₂O, absolute frequency): δ=25.56 (t, 2C), 32.33 (t, 1C), 54.11 (tt, 1C), 57.05 (t, 2C) and 74.79 (t, J=140 Hz, 1C) ppm.

EXAMPLE 3

Disodium 1-hydroxy-3-(1′-pyrrolidinyl)-propylidene-1,1-bisphosphonate, trihydrate 2N Sodium hydroxide (103.7 ml) was added to a stirred suspension of 1-hydroxy-3-(1′-pyrrolidinyl)-propylidene-1,1-bisphosphonic acid (30 g) in water (120 ml). Ethanol (225 ml) was added with stirring to the resulting solution to give a crystalline precipitate. The crystals were collected by filtration, washed with ethanol and dried in the air.

Microanalysis:
Calc.: C: 21.71; H: 5.47; N: 3.62; P: 16.00: H₂O: 13.96
Found: C: 21.66; H: 5.47; N: 3.61; P: 15.91: H₂O: 14.08

¹H-NMR (D₂O, HDO=4.66 ppm as reference): δ=1.90 (bm, 4H), 2.15 (m, 2H), 2.86 (bm, 2H), 3.29 (t, 2H), and 3.53 (bm, 2H) ppm.

¹³C-NMR (D₂O, absolute frequency): δ=20.72 (2C), 27.63 (1C), 49.62 (t, J=7 Hz, 1C), 51.70 (2C) and 70.34 (t, J=127 Hz, 1C) ppm.

EXAMPLE 4

3-(3′-Methyl-1′-pyrrolidinyl)-propanoic acid, hydrochloride

3-Methylpyrrolidine (45 ml) was added slowly with stirring to methyl acrylate (50 ml). When the exothermic reaction had ceased, the product was distilled in vacuo.

The pure methyl 3-(3′-methyl-1′-pyrrolidinyl)-propanoate was refluxed for 3 hours with an excess of 20% hydrochloric acid. Evaporation to dryness in vacuo and stirring with acetone gave the title compound as colourless crystals.

M.p. 163°–164° C.

¹H-NMR (NaOD, HDO=4.66 ppm as reference): δ=0.91 (d, 3H), 1.35 (m, 1H), 1.96 (m, 1H), 2.20 (m, 1H), 2.32 (m, 3H), 2.70–2.90 (m, 4H) and 3.00 (m, 1H) ppm.

¹³C-NMR (NaOD, absolute frequency): δ=21.13 (q, 1C), 34.13 (d, 1C), 34.29 (t, 1C), 37.68 (t, 1C), 55.11 (t, 1C), 56.25 (t, 1C), 63,18 (t, 1C) and 182.64 (s, 1C) ppm.

EXAMPLE 5

1-Hydroxy-3-(3′-methyl-1′-pyrrolidinyl)-propylidene-1,1-bisphosphonic acid 3-(3′-methyl-1′-pyrrolidinyl)-propanoic acid, hydrochloride (9.6 g) and phosphorous acid (8 g) were heated at 140° C. until a clear solution was formed. After cooling to 80° C. phosphorus trichloride (15 ml) was added dropwise, and the resulting mixture was heated at 85°–90° C. overnight. Excessive phosphorus trichloride was removed in vacuo, and the residue was refluxed with water (60 ml) for 4 hours. After removal of the solvent in vacuo, the residue was crystallized from ethanol to yield the title compound with melting point 225° C. (dec.).

¹H-NMR (NaOD, HDO=4.66 ppm as reference); δ=0.88 (d, 3H), 1.42 (m, 1H), 2.00 (m, 3H), 2.20 (m, 1H), 2.45 (m, 1H), 219–3.20 (m, 5H), ppm.

¹³C-NMR (NaOD, absolute frequency): δ=20.63 (1C), 34.17 (1C), 34.32 (1C), 34.69 (1C), 54.84 (1C), 55.82 (1C), 62.66 (1C) and 77.56 (t, J=135 Hz, 1C) ppm.

EXAMPLE 6

3-(2′-Methyl-1′-pyrrolidinyl)-propanoic acid, hydrochloride

A mixture of ethyl 3-(2′-methyl-1′-pyrrolidinyl)-propanoate (110 g) and 6N hydrochloric acid (350 ml) was refluxed for 4 hours. After cooling and evaporation to dryness in vacuo, the residue was stirred with acetone to yield the title compound in the form of colourless crystals with melting point 144°–145° C.

¹H-NMR (D₂O, HDO=4.66 ppm as reference): δ=1.31 (d, 3H), 1.60 (m, 1H), 1.86–2.05 (m, 2H), 2.20 (m, 1H), 2.73 (m, 2H), 2.95–3.15 (m, 2H), 3.32 (m, 1H), and 3.55 (m, 2H) ppm.

EXAMPLE 7

1-Hydroxy-3-(2′-methyl-1′-pyrrolidinyl)-propylidene-1,1-bisphosphonic acid

This compound was prepared from 3-(2′-methyl-1′-pyrrolidinyl)-propanoic acid, hydrochloride by following the procedure described in Example 5. Crystallization from ethanol gave the title compound with m.p. 230° C. (dec.).

¹H-NMR (D₂O, HDO=4.66 ppm as reference: δ=1.26 (d, 3H), 1.55 (m, 1H), 1.8–2.0 (m, 2H), 2.05–2.35 (m, 3H), 3.02 (m, 2H), 3.30 (m, 1H), 3.55–3.70 (m, 2H) ppm.

¹³C-NMR (D₂O, absolute frequency): δ=18.21 (1C), 23.73 (1C) 31.79 (1C), 33.54 (1C), 51.80 (1C), 55.98 (1C), 67.60 (1C), and 74.27 (t, J=141 Hz, 1C) ppm.

EXAMPLE 8

The compounds mentioned below are prepared by substituting the appropriate mono-, di- or trialkylsubstituted pyrrolidine for 3-methylpyrrolidine in Example 4 and following the procedures described herein. In case of 2,5-disubstituted pyrrolidines the reaction with methyl acrylate is slow and may require heating for several hours. The intermediates thus prepared are subsequently transformed into the following bisphosphonic acids by using the procedures described in Example 2 or Example 5:

1-Hydroxy-3-(2′,3′-dimethyl-1′-pyrrolidinyl)-propylidine-1,1-bisphosphonic acid;
1-Hydroxy-3-(2′,4′-dimethyl-1′-pyrrolidinyl)-propylidine-1,1-bisphosphonic acid;
1-Hydroxy-3-(2′,5′-dimethyl-1′-pyrrolidinyl)-propylidine-1,1-bisphosphonic acid;
1-Hydroxy-3-(2′,2′-dimethyl-1′-pyrrolidinyl)-propylidine-1,1-bisphosphonic acid;
1-Hydroxy-3-(3′,3′-dimethyl-1′-pyrrolidinyl)-propylidine-1,1-bisphosphonic acid;
1-Hydroxy-3-(3′,4′-dimethyl-1′-pyrrolidinyl)-propylidine-1,1-bisphosphonic acid;
1-Hydroxy-3-(2′,2′,3′-trimethyl-1′-pyrrolidinyl)-propylidine-1,1-biphosphonic acid;
1-Hydroxy-3-(2′,2′,4′-trimethyl-1′-pyrrolidinyl)-propylidine-1,1-biphosphonic acid;
1-Hydroxy-3-(2′,2′,5′-trimethyl-1′-pyrrolidinyl)-propylidine-1,1-biphosphonic acid;
1-Hydroxy-3-(2′,3′,5′-trimethyl-1′-pyrrolidinyl)-propylidine-1,1-biphosphonic acid;
1-Hydroxy-3-(2′,4′,4′-trimethyl-1′-pyrrolidinyl)-propylidine-1,1-bisphosphonic acid;

1-Hydroxy-3-(2'-ethyl-1'-pyrrolidinyl)-propylidine-1,1-bisphosphonic acid;
1-Hydroxy-3-(3'-ethyl-1'-pyrrolidinyl)-propylidine-1,1-bisphosphonic acid;
1-Hydroxy-3-(3',3'-diethyl-1'-pyrrolidinyl)-propylidine-1,1-bisphosphonic acid;
1-Hydroxy-3-(3',4'-diethyl-1'-pyrrolidinyl)-propylidine-1,1-bisphosphonic acid;
1-Hydroxy-3-(2',3',4'-triethyl-1'-pyrrolidinyl)-propylidine-1,1-bisphosphonic acid;
1-Hydroxy-3-(2'-propyl-1'-pyrrolidinyl)-propylidine-1,1-bisphosphonic acid
1-Hydroxy-3-(3'-propyl-1'-pyrrolidinyl)-propylidine-1,1-bisphosphonic acid;
1-Hydroxy-3-(2',2'-dipropyl-1'-pyrrolidinyl)-propylidine-1,1-bisphosphonic acid;
1-Hydroxy-3-(2'-butyl-1'-pyrrolidinyl)-propylidine-1,1-bisphosphonic acid;
1-Hydroxy-3-(3'-butyl-1'-pyrrolidinyl)-propylidine-1,1-bisphosphonic acid;
1-Hydroxy-3-(2'-sec.butyl-1'-pyrrolidinyl)-propylidine-1,1-bisphosphonic acid;
1-Hydroxy-3-(2'-isobutyl-1'-pyrrolidinyl)-propylidine-1,1-bisphosphonic acid;
1-Hydroxy-3-(2'-hexyl-1'-pyrrolidinyl)-rpopylidine-1,1-bisphosphonic acid;
1-Hydroxy-3-(1'-cis-octahydroindolyl)-propylidine-1,1-bisphosphonic acid;
1-Hydroxy-3-(1'-trans-octahydroindolyl)-propylidine-1,1-bisphosphonic acid;
1-Hydroxy-3-(2'-cis-octahydroixoindolyl)-propylidine-1,1-bisphosphonic acid.

What we claim is:

1. A compound of the formula I

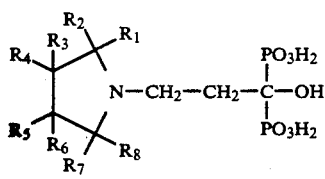

(I)

in which $R_1$–$R_8$ can be the same or different and stand for hydrogen or a straight or branched aliphatic $C_1$–$C_{10}$ hydrocarbon radical, or pharmaceutically acceptable salts thereof.

2. A compound according to claim 1, in which $R_1$–$R_8$, being the same or different, each stands for hydrogen or $C_1$–$C_4$-alkyl.

3. A salt according to claim 1, which is a salt of a compound of formula I with a pharmaceutically acceptable non-toxic base, such salt being selected from the group consisting of alkali metal salts, alkaline earth metal salts, and salts with ammonia or suitable non-toxic amines.

4. A compound of formula I according to claim 1, selected from the group consisting of
1-Hydroxy-3-(1'-pyrrolidinyl)-propylene-1,1-bisphosphonic acid,
1-Hydroxy-3-(3'-methyl-1'-pyrrolidinyl)-propylidene-1,1-bisphosphonic acid,
1-Hydroxy-3-(2'-methyl-1'-pyrrolidinyl)-propylidene-1,1-bisphosphonic acid;
and salts thereof.

5. A compound according to claim 4, which is the disodium salt of 1-hydroxy-3-(1'-pyrrolidinyl)-propylidene-1,1-bisphosphonic acid.

6. A compound according to claim 5, which is the trihydrate of the disodium salt of 1-hydroxy-3-(1'-pyrrolidinyl)-propylidene-1,1-bisphosphonic acid.

7. A pharmaceutical composition containing an effective amount of one or more of the compounds of claim 1, together with pharmaceutically acceptable, non-toxic carriers and/or auxiliary agents.

8. A pharmaceutical composition according to claim 7 containing 0.25 mg–16 mg of the active ingredient when to be given parenterally, and 3 ms –600 mg when to be given orally.

9. A method for the treatment of a patient suffering from osteoporosis, rheumatoid arthritis, atherosclerosis, hypercalcemia due to malignancies or primary hyperparathyroidism, Pagets disease, or pathological condition characterized by an abnormal calcium balance, in which a composition according to claim 7 is administered to the patient in need of treatment.

* * * * *